United States Patent
Luo et al.

(10) Patent No.: US 11,982,608 B2
(45) Date of Patent: May 14, 2024

(54) METHOD FOR TESTING SURFACE ENERGY OF AGGREGATE BASED ON STATIC DROP METHOD

(71) Applicant: WUHAN UNIVERSITY OF TECHNOLOGY, Wuhan (CN)

(72) Inventors: Rong Luo, Wuhan (CN); Jing Luo, Wuhan (CN); Chongzhi Tu, Wuhan (CN); Tingting Huang, Wuhan (CN); Xiang Wang, Wuhan (CN); Longchang Niu, Wuhan (CN); Qiang Miao, Wuhan (CN)

(73) Assignee: WUHAN UNIVERSITY OF TECHNOLOGY, Wuhan (CN)

( * ) Notice: Subject to any disclaimer, the term of this patent is extended or adjusted under 35 U.S.C. 154(b) by 89 days.

(21) Appl. No.: 17/826,171

(22) Filed: May 27, 2022

(65) Prior Publication Data
US 2023/0017016 A1  Jan. 19, 2023

(30) Foreign Application Priority Data

Jul. 15, 2021  (CN) .......................... 202110802076.6

(51) Int. Cl.
*G01N 13/02*  (2006.01)

(52) U.S. Cl.
CPC ..... *G01N 13/02* (2013.01); *G01N 2013/0208* (2013.01)

(58) Field of Classification Search
CPC .......... G01N 2013/0208; G01N 13/02; G01N 2013/0283; G01N 33/42; G01N 13/00
See application file for complete search history.

(56) References Cited

FOREIGN PATENT DOCUMENTS

| CN | 103852403 A | | 6/2014 | |
|----|----|----|----|----|
| CN | 106918553 A | | 7/2017 | |
| CN | 108181211 A | * | 6/2018 | ............. G01N 15/00 |

(Continued)

OTHER PUBLICATIONS

Masad, Eyad, et al. "Viscoplastic modeling of asphalt mixes with the effects of anisotropy, damage and aggregate characteristics." Mechanics of Materials 37.12 (2005): 1242-1256. (Year: 2005).*

(Continued)

*Primary Examiner* — Kristina M Deherrera
*Assistant Examiner* — Fatemeh Esfandiari Nia

(57) ABSTRACT

Disclosed is a method for measuring surface energy of aggregates based on static drop method, comprising (1) aggregates grinding and pretreatment; (2) obtaining the surface texture index; (3) calculating the surface energy based on static drop method experiment; (4) fitting to obtain a functional relationship between the surface texture index and surface energy; (5) calculating the surface energy of the original aggregate. The method considers the influence of the grinding process on the surface texture of the aggregates when measuring the surface energy of the aggregates, which significantly improves the accuracy of the static drop method test. The static drop method can be used to replace the vapor adsorption method to test the surface energy of aggregate, and the low-cost optical contact angle instrument can replace the expensive magnetic suspension weight balance system to test the surface energy of aggregate, which greatly reduces the test cost.

8 Claims, 2 Drawing Sheets

(a)

(b)

(c)

(56) References Cited

FOREIGN PATENT DOCUMENTS

| | | | | |
|---|---|---|---|---|
| CN | 108562727 A | * | 9/2018 | |
| CN | 109580407 A | * | 4/2019 | ............... G01N 3/56 |
| CN | 112284980 A | | 1/2021 | |
| EP | 3282224 A | | 2/2018 | |
| JP | 2003270117 A | | 9/2003 | |

OTHER PUBLICATIONS

Zollinger, Corey James. Application of surface energy measurements to evaluate moisture susceptibility of asphalt and aggregates. Diss. Texas A&M University, 2005. (Year: 2005).*
Masad, Eyad, and Thomas Fletcher. Aggregate imaging system (AIMS): Basics and applications. No. FHAWA/TX-05/5-1707-01-1. Texas Transportation Institute, Texas A & M University System, 2005. (Year: 2005).*
Dalton, Laura E., et al. "Contact angle measurements using sessile drop and micro-CT data from six sandstones." Transport in Porous Media 133 (2020): 71-83. (Year: 2020).*
CN-109580407-A—Translate (Year: 2019).*
CN-108562727-A—translate (Year: 2019).*
CN-108181211-A—translate (Year: 2018).*
Journal of Chongqing Jiaotong University (from Natural Science Edition) vol. 31, No. Phase 3, Issue date Jun. 30, 2012.
"Journal of Wuhan University of Technology" General Science and Engineering Edition), p. 44 vol. 2, Issue date May 31, 2020.

* cited by examiner

METHOD FOR TESTING SURFACE ENERGY OF AGGREGATE BASED ON STATIC DROP METHOD

FIELD OF THE DISCLOSURE

The disclosure relates to the technical field of road engineering, in particular to a method for testing surface energy of aggregate based on static drop method.

BACKGROUND

In engineering practice, it is found that diseases such as loosening, spalling, and cracking are prone to occur during the service process of asphalt pavement. Relevant studies have shown that these diseases are related to insufficient adhesion between asphalt and aggregate. The surface energy theory commonly used in the world accurately and quantitatively evaluates the adhesion between asphalt and aggregates from the microscopic point of view of intermolecular interactions, so this theoretical method can be used to evaluate the performance of asphalt mixture material. Before using the surface energy theory to calculate the asphalt-aggregate adhesion index and evaluate the performance of the asphalt mixture, it is necessary to conduct experiments to obtain the surface energy of the aggregate.

In the prior art, the surface energy of aggregate is often tested by using vapor adsorption method or static drop method, wherein vapor adsorption method test result is accurate and highly automated, but its instrument is very expensive so that the condition of this test is high, test resources are scarce, and there are strict requirements on the particle size of aggregates. In contrast, the static drop method is used to test the surface energy parameters of aggregates. The test principle is simple, and the requirements for the particle size of the aggregates are low. The most important thing is that the test instrument is more conventional and the test is easier to carry out. However, in practice, a large number of experimental data show that when the same aggregate is tested by the vapor adsorption method and the static drop method, the accuracy and stability of the obtained test results are quite different. The reason is that the aggregate needs to be smoothed before the static drop test, which will directly destroy the surface texture of the aggregate, while the surface energy of the aggregate is not required to be smoothed by the vapor adsorption method. Therefore, the test results of the vapor adsorption method include the influence factor of the surface texture of the aggregate. Therefore, it is necessary to comprehensively consider the actual test requirements in terms of test cost, experimental feasibility, and test accuracy, in order to propose a more effective low-cost aggregate surface energy test method.

SUMMARY

To achieve the above technical purpose, this disclosure provides a test method of aggregate surface energy based on static drop method to solve the problem that the surface texture factor of aggregate is not considered in the test of aggregate surface energy by the traditional static drop method, resulting in a large difference between the test results of the traditional static drop method and those of the vapor adsorption method.

This disclosure provides a method for testing surface energy of aggregate based on static drop method, comprising the following steps:

(1) aggregates grinding and pretreatment: dividing the original aggregates into two groups, one group is subjected to surface grinding and pretreatment and recorded as polished aggregate, and the other group is not treated and recorded as original aggregate;

(2) obtaining the surface texture index: testing the surface texture of the original aggregate and the polished aggregate, and obtaining the surface texture index of the original aggregate and the surface texture index of the polished aggregate, respectively;

(3) calculating the surface energy based on static drop method experiment: using static drop method to test contact angle of the polished aggregate, and calculating the surface energy of the polished aggregate;

(4) fitting to obtain a functional relationship between the surface texture index and surface energy: performing fitting based on the surface texture index of the polished aggregate and the surface energy of the polished aggregate, and obtaining a functional relationship between the surface texture index and the surface energy;

(5) calculating the surface energy of the original aggregate: bring the surface texture index of the original aggregate into the functional relationship between the surface texture index and the surface energy to obtain the surface energy of the original aggregate considering the factors affecting the surface texture.

The beneficial effects of this disclosure include: this disclosure provides a method for measuring surface energy of aggregates based on static drop method. The method considers the influence of the grinding process on the surface texture of the aggregates when measuring the surface energy of the aggregates, which significantly improves the accuracy of the static drop method test. The static drop method can be used to replace the vapor adsorption method to test the surface energy of aggregate, and the low-cost optical contact angle instrument can replace the expensive magnetic suspension weight balance system to test the surface energy of aggregate, which greatly reduces the test cost.

BRIEF DESCRIPTION OF THE DRAWINGS

Accompanying drawings are for providing further understanding of embodiments of the disclosure. The drawings form a part of the disclosure and are for illustrating the principle of the embodiments of the disclosure along with the literal description. Apparently, the drawings in the description below are merely some embodiments of the disclosure, a person skilled in the art can obtain other drawings according to these drawings without creative efforts. In the figures.

DETAILED DESCRIPTION OF PREFERRED EMBODIMENTS

Figure 1:
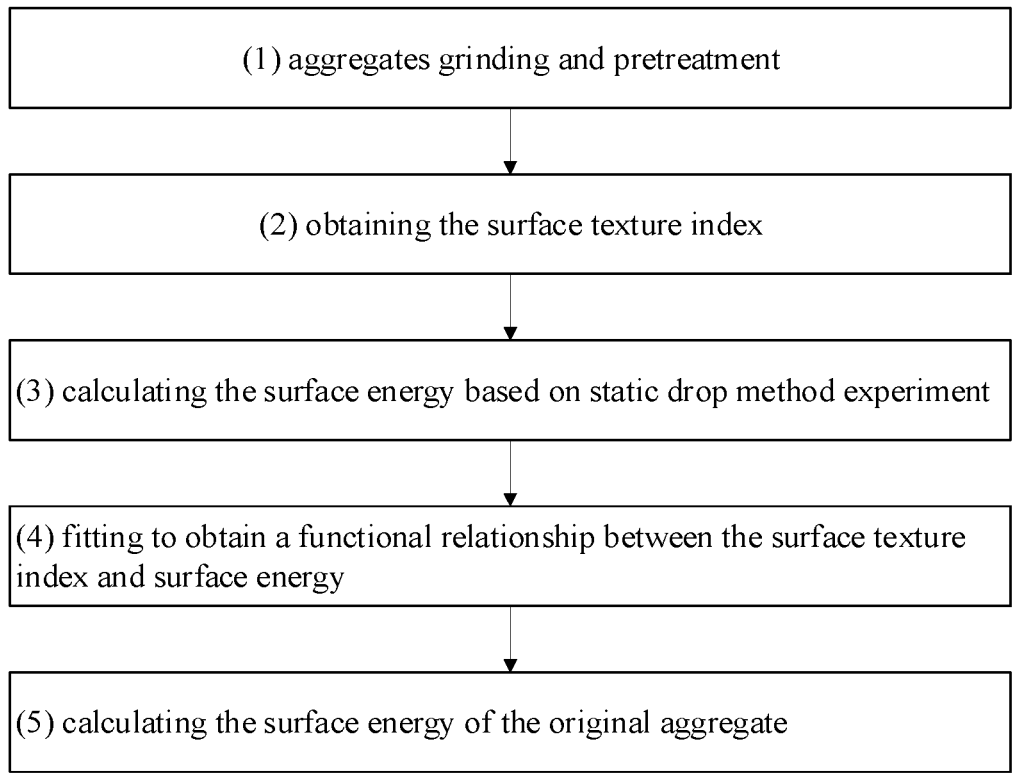
FIG. 1 is a flow chart of the method for testing surface energy of aggregate based on static drop method in this disclosure.
Figure 2:
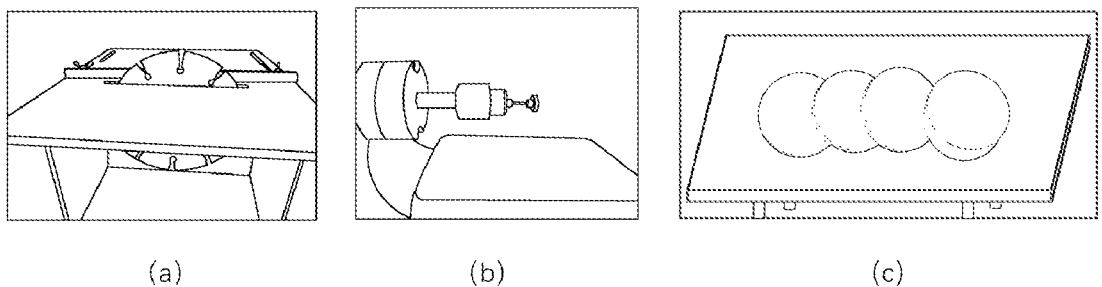
FIG. 2 is tools for surface machining.

Please refer to FIG. 1, FIG. 1 is a flow chart of an embodiment of the method for testing the surface energy of aggregates based on the static drop method of this disclosure. The method for testing the surface energy of aggregates based on the static drop method in this disclosure comprises the following steps:

(1) Aggregates grinding and pretreatment: dividing the original aggregates into two groups, one group is subjected to surface grinding and pretreatment and recorded as polished aggregate, and the other group is not treated and recorded as original aggregate; both the original aggregate and the polished aggregate contain several aggregate samples with the same initial particle size; the surface grinding method of the grinding aggregate is any one, two, or three of cutting saw grinding, grinding wheel grinding and sandpaper grinding, as shown in FIG. 2, the grinding time of each surface grinding method is more than 30s, and the grinding degree of each aggregate sample in the polished aggregate is the same. However, due to the difference of the grinding tools, the polished aggregate presents three kinds of surfaces with different roughness, so that the subsequent surface texture index of the grinding aggregate presents differentiated data. Specifically, the steps of the pretreatment are: after the surface of the polished aggregate is polished, rinsing it with distilled water until no sediment is attached to the surface, and drying the cleaned aggregate sample at 110-120° C.

Figure 3:
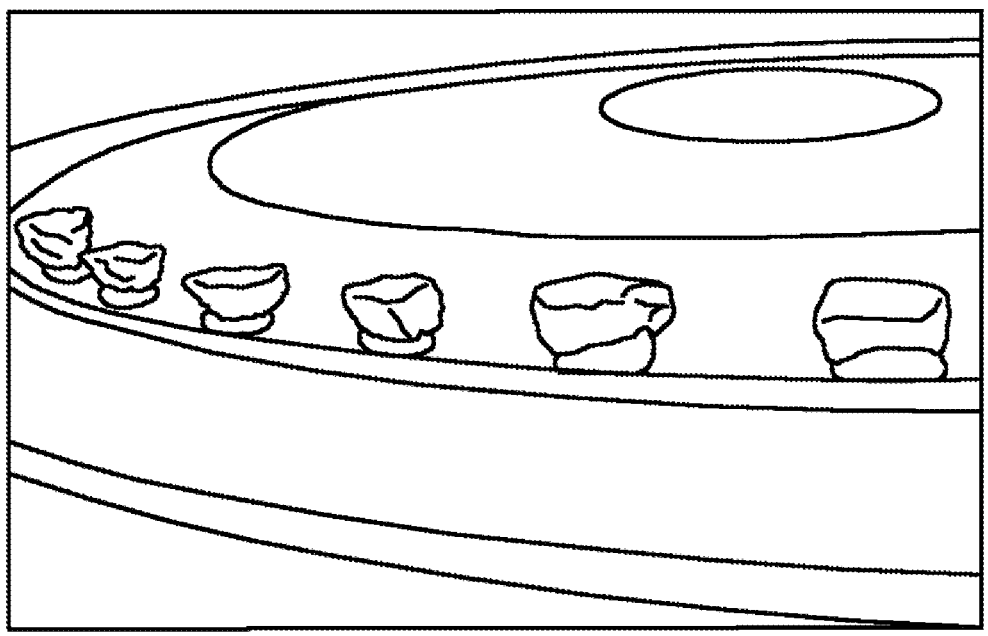
FIG. 3 is placement of aggregate sample on the tray.

(2) Obtaining the surface texture index. In this step, it is necessary to obtain the surface texture index of the original aggregate and the surface texture index of the polished aggregate, as shown in FIG. 3; in one hand, fixing the aggregate sample of the original aggregate on the aggregate tray of AIMS system, using the AIMS system to test the surface texture of the aggregate sample of the original aggregate, and calculating the surface texture index of the original aggregate after averaging the test results; on the other hand, fixing the aggregate samples of the polished aggregate on the aggregate tray, and photograph the polished surfaces of the aggregate samples of each surface polishing method respectively; after taking the average of the shooting results, calculating the surface texture index of the grinding aggregate for each surface grinding method separately.

In this embodiment, viscous materials such as rubber mud are used to fix aggregate samples to ensure the stability of aggregate samples during data collection; the image data of surface texture is collected by using the Aggregate Image Measurement System (AIMS) instrument. The surface texture index of multiple aggregate samples obtained by AIMS under the same surface grinding method is taken as the average value, and the surface texture index of multiple aggregate samples in the original aggregate is taken as the average value. The surface texture index of the polished aggregate under the three methods of cutting saw grinding, grinding wheel grinding, and sandpaper grinding, and the surface texture index of the original aggregate are obtained. At this point, the surface texture index of grinding aggregate under three grinding methods characterizes the surface texture state of aggregate under different roughness, while the surface texture index of original aggregate characterizes the surface texture state of aggregate under original roughness.

(3) Calculating the surface energy based on static drop method experiment.

In this step, firstly, using static drop method to test contact angle of the polished aggregate, and the specific steps are as follows:

1) 30 minutes before the start of the experiment, starting the optical contact angle instrument, the supporting constant temperature water bath system, and the micro-compressor for preheating, so that the temperature in the test chamber of the optical contact angle meter is stabilized at about 20° C.; the polished aggregate is evenly fixed in the test chamber, viscous materials such as rubber mud can be selected to fix the non-grinding surface of the polished aggregate, so that the grinding surface is vertically upward, and the grinding surface of each aggregate sample in the polished aggregate is set to the camera of the optical contact angle meter.

2) Adjusting the reagent needle to a preset position, drawing the test reagent into a needle tube, moving the position of the reagent needle until a distance of a drop is maintained between the needle and the aggregate sample, and both the needle and the aggregate sample appear in the camera picture; controlling the pressure of the needle tube, so that different test reagents release droplets of the same volume, and the released droplets are attached to the tip of the needle, wherein the different test reagents included distilled water, formamide, and ethylene glycol, so that the preferred test reagent contains both polar and non-polar solvents, and each needle released a droplet of one test reagent.

3) Moving the test chamber so that each aggregate sample corresponds to receive one of the released droplets.

4) Testing the contact angle between each aggregate sample and the received droplet for a preset test time. On the surface of the aggregate sample, the intersection of the received droplet and its projection is set as the baseline, and using an optical contact angle meter to measure the angle between the tangent at the intersection of the droplet profile and the baseline, which is recorded as contact angle, obtaining the contact angles between the polished aggregate and different test reagents. Among them, the preset test time is different for different test reagents; the optimal dosage of the three reagents is 1 µL, and the preset test time of contact angle is 10-30 s when distilled water was used as the test reagent. When using formamide or ethylene glycol as test reagent, the preset test time of contact angle is more than 20 s.

Then, the surface energy of the polished aggregate is calculated according to the contact angle of the polished aggregate. The specific calculation steps are as follows:

Bringing the contact angles between the polished aggregate and three different test reagents into the Young-Dupre equation, and obtaining the surface energy parameter by using programming solution, the surface energy of the polished aggregate is calculated as:

$$2(\sqrt{\gamma_S^{LW}\gamma_L^{LW}} + \sqrt{\gamma_S^+\gamma_L^-} + \sqrt{\gamma_S^-\gamma_L^+}) = \gamma_L(1+\cos\theta) \quad (1)$$

where the surface energy parameters include $\gamma_S^{LW}$, $\gamma_L^{LW}$, $\gamma_S^+$, $\gamma_S^-$, $\gamma_L^+$, $\gamma_L^-$, and $\gamma_L$, among which $\gamma_S^{LW}$ is the non-polar component of the surface energy of solid material, $\gamma_L^{LW}$ is the non-polar component of the surface energy of liquid material, $\gamma_S^+$ is the polar acid component of the surface energy of solid material, $\gamma_S^-$ is the polar alkali component of the surface energy of solid material, $\gamma_L^+$ is the polar acid component of the surface energy of liquid material, $\gamma_L^-$ is the polar alkali component of the surface energy of the liquid material, $\gamma_L$ is the surface tension of the liquid with a unit of erg/cm², $\theta$ is the contact angle between the solid-liquid-gas phase.

(4) Fitting to obtain a functional relationship between the surface texture index and surface energy. In this step, performing fitting based on the surface texture index of the polished aggregate and the surface energy of the polished aggregate, and obtaining a functional relationship between the surface texture index and the surface energy, and the surface energy by fitting are:

$$\gamma = Ae^{Kx} \quad (2)$$

where γ is aggregate surface energy considering the influence of surface texture, the unit is erg/cm², x is the surface texture index of the aggregate; A is the surface energy corresponding to the surface texture index of the aggregate in the state of x=0, the unit is erg/cm²; K is a constant that determines the influence of the surface texture on the surface energy; in the exponential fitting process, obtaining parameters A and K, and determining the functional relationship between the surface texture index and surface energy.

(5) Calculating the surface energy of the original aggregate. In this step, bringing the surface texture index of the original aggregate in step (2) into the functional relationship between the surface texture index and the surface energy in step (4) to obtain the surface energy of the original aggregate considering the factors affecting the surface texture.

The effect of the above-mentioned aggregate surface energy testing method based on static drop method will be described below through specific embodiments.

Embodiment 1

(1) Selecting Four Kinds of Aggregate for Grinding and Pretreatment.

Four kinds of aggregates from Hubei Province, China and Guangdong Province, China were selected as test materials in this embodiment, including granite, diabase, basalt, and limestone. The four kinds of aggregates were sieved to obtain samples with a particle size of 13.2-16 mm, 80 samples for each aggregate; in each aggregate, 20 samples were not treated as the original aggregate, and the other 60 samples were used as polished aggregate. The aggregate samples were grinded by cutting saw, grinding wheel, and sandpaper. Each grinding method grinds 20 samples as parallel test, and the processing time is more than 30 s. The four kinds of aggregate samples after grinding are classified according to different grinding methods, and the distilled water is used to rinse continuously until there is no sediment on the surface, and the washed water is clear and free of impurities. The washed polished aggregate is placed in 120° C. oven for 4 h, and the water is dried.

(2) Obtaining the Surface Texture Index of these Four Kinds of Aggregates.

Selecting a 12.5 mm aggregate tray, and placing the treated 20 aggregate samples of each aggregate by grinding method in the groove of the aggregate tray, and the aggregate samples were fixed with rubber mud to make the grinding side faces upwards horizontally; placing the aggregate tray with the fixed aggregate sample into the AIMS instrument to ensure that the camera can be aligned to the grinding plane. Measuring the surface texture index of multiple aggregate samples for each aggregate and taking the average value. Obtaining the surface texture index of the polished aggregate and the surface texture index of the original aggregate in three ways: cutting saw grinding, grinding wheel grinding and sandpaper grinding.

(3) Calculating Surface Energy of Four Aggregates Based on Static Drop Method.

For the four aggregates treated by different grinding methods, the contact angles of the aggregates with distilled water, formamide, and ethylene glycol are tested by static drop method, and each test reagent releases 1 μL; each aggregate was subjected to five parallel tests with a grinding method, and the average value was taken as the contact angle result. Then, the contact angles measured by the aggregate samples of each aggregate using the same grinding method and the three reagents are brought into the Young-Dupre equation shown in formula (1) to calculate the surface energy; in this way, the surface energy of four kinds of aggregates can be obtained by three grinding methods.

(4) Obtaining the Functional Relationship Between Surface Texture Index and Surface Energy by Fitting, and Calculating the Surface Energy of Four Kinds of Original Aggregates.

Figure 4:
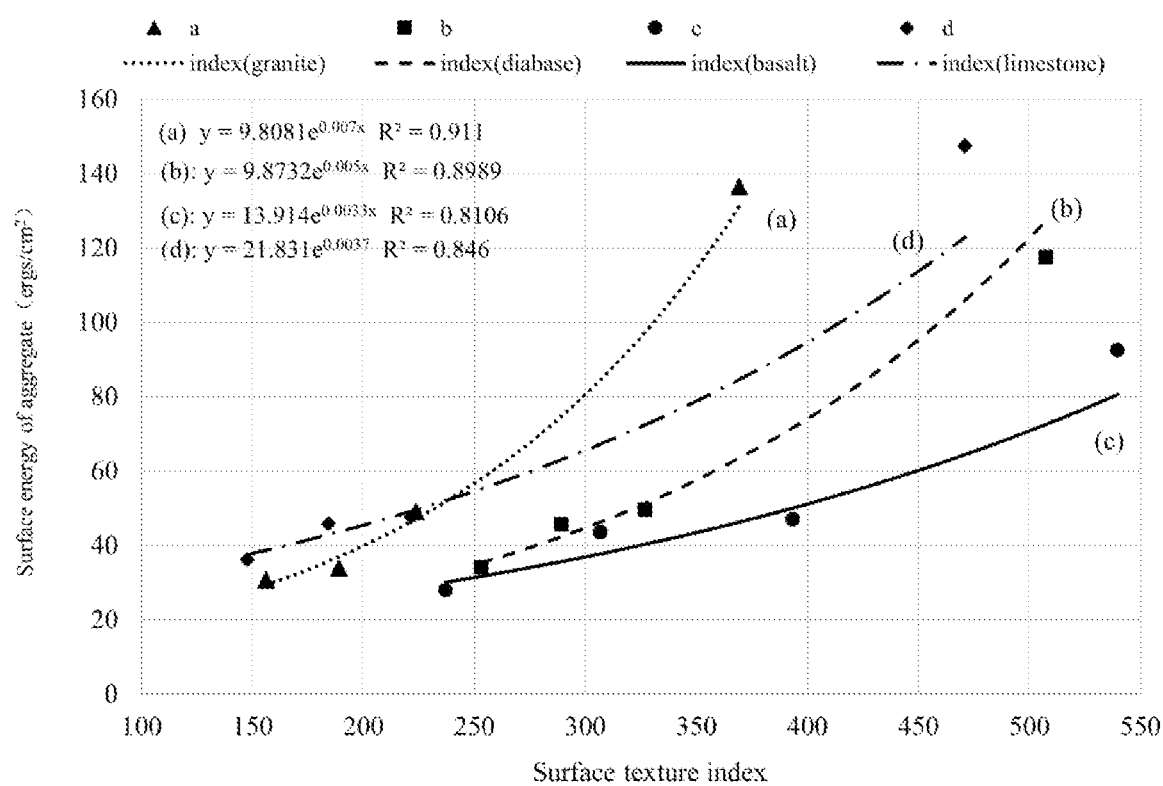
FIG. 4 is the fitting curve and function relationship between surface texture index and surface energy of four kinds of aggregates in Embodiment 1 of this disclosure.

For each aggregate, fitting the surface texture value of the polished aggregate and the surface energy value of the polished aggregate by the model shown in formula (2), and calculating the values of parameters A and K, thus the functional relationship between the surface texture index and the surface energy is determined, and the fitting curve corresponding to the functional relationship covers the surface texture index of the original aggregate. Repeating this method to fit each aggregate, and obtaining the functional relationship between the surface texture index and surface energy of four kinds of aggregates respectively. The specific fitting curves are shown in FIG. 4. The fitting curves of granite, diabase, basalt, and limestone correspond to the four curves of a, b, c, and d in FIG. 4.

The surface texture indices of the original four kinds of aggregates obtained above are respectively put into the corresponding functional equations, and the surface energy of the four kinds of aggregates considering the influence factors of surface texture is calculated. These four kinds of aggregates used in this embodiment were tested by the traditional vapor adsorption method. The comparison results are shown in Table 1.

TABLE 1

Surface energy of four aggregates obtained by the test method of this disclosure and by traditional vapor adsorption method

| Aggregate type | Surface energy calculated by fitting (erg/cm²) | Surface energy obtained by vapor adsorption method (erg/cm²) | Difference rate (%) |
| --- | --- | --- | --- |
| granite | 129.96 | 136.39 | 4.71 |
| diabase | 124.97 | 117.34 | −6.50 |
| basalt | 82.65 | 92.45 | 10.60 |
| limestone | 124.74 | 147.40 | 15.37 |

It can be seen from the comparison results in Table 1 that the surface energy results obtained by the test method of this disclosure and the traditional vapor adsorption method for the four aggregates are very close, and the overall difference rate is below 16%, especially for the test of granite and diabase, the difference rate is controlled below 10%, which has a good test effect; furthermore, the test method of this disclosure can replace the traditional vapor adsorption method. On the one hand, the test method of this disclosure takes into account the influence factors of surface texture, and can obtain more accurate test results. On the other hand, replacing the high-cost vapor adsorption method with the low-cost static drop method can significantly reduce the cost, thereby achieving the effect of obtaining higher test accuracy at a lower test cost.

Different from the existing technology, this disclosure provides a test method of aggregate surface energy based on static drop method. In this method, the influence of grinding treatment on the surface texture of aggregate is considered when measuring the surface energy of aggregate, which obviously improves the accuracy of static drop method. The static drop method can be used to replace the vapor adsorption method to test the surface energy of aggregate, and the low-cost optical contact angle instrument can replace the expensive magnetic suspension weight balance system to test the surface energy of aggregate, which greatly reduces the test cost.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A method for testing surface energy of aggregate based on static drop method, comprising the following steps:
   (1) aggregates grinding and pretreatment: dividing the original aggregates into two groups, one group is subjected to surface grinding and pretreatment and recorded as polished aggregate, and the other group is not treated and recorded as original aggregate;
   (2) obtaining the surface texture index: testing the surface texture of the original aggregate and the polished aggregate to obtain the surface texture index of the original aggregate and the surface texture index of the polished aggregate, respectively;
   wherein testing the surface texture of the original aggregate and the polished aggregate comprises:
      fixing aggregate sample of the original aggregate on aggregate tray of AIMS system, using the AIMS system to test the surface texture of the aggregate sample of the original aggregate, and calculating the surface texture index of the original aggregate after averaging test results;
      fixing aggregate samples of the polished aggregate on the aggregate tray, and photograph polished surfaces of the aggregate samples of the polished aggregate: after taking the average of shooting results, calculating the surface texture index of the polished aggregate:
   (3) calculating the surface energy based on static drop method experiment: using static drop method to test contact angle of the polished aggregate, and calculating the surface energy of the polished aggregate;
   wherein on a surface of the aggregate sample of the polished aggregate, an intersection of a droplet received by the surface and a projection of the received droplet is defined as a baseline, an angle between a tangent at the intersection of the droplet and the baseline is defined as the contact angle;
   wherein calculating the surface energy of the polished aggregate comprises:
      bringing the contact angle into the Young-Dupre equation; and
      obtaining the surface energy parameters by using programming solution;
   wherein the surface energy of the polished aggregate is calculated as:

$$2(\sqrt{\gamma_S^{LW}\gamma_L^{LW}}+\sqrt{\gamma_S^+\gamma_L^-}+\sqrt{\gamma_S^-\gamma_L^+})=\gamma_L(1+\cos\theta);$$

wherein the surface energy parameters include $\gamma_S^{LW}$, $\gamma_L^{LW}$, $\gamma_S^+$, $\gamma_S^-$, $\gamma_L^+$, $\gamma_L^-$, and $\gamma_L$, among, $\gamma_S^{LW}$ is the non-polar component of the surface energy of solid material, $\gamma_L^{LW}$ is the non-polar component of the surface energy of liquid material, $\gamma_S^+$ is the polar acid component of the surface energy of solid material, $\gamma_S^-$ is the polar alkali component of the surface energy of solid material, $\gamma_L^+$ is the polar acid component of the surface energy of liquid material, $\gamma_L^-$ is the polar alkali component of the surface energy of the liquid material, $\gamma_L$ is the surface tension of the liquid with a unit of erg/cm², θ is the contact angle between the solid-liquid-gas phase;
   (4) fitting to obtain a functional relationship between the surface texture index and surface energy: performing fitting based on the surface texture index of the polished aggregate and the surface energy of the polished aggregate, and obtaining a functional relationship between the surface texture index of the polished aggregate and the surface energy of the polished aggregate;
   (5) calculating the surface energy of the original aggregate: bringing the surface texture index of the original aggregate into the functional relationship between the surface texture index of the polished aggregate and the surface energy of the polished aggregate to obtain the surface energy of the original aggregate.

2. The method for testing surface energy of aggregate based on static drop method according to claim 1, wherein the original aggregate and the polished aggregate both contain several aggregate samples with the same initial particle size;
   the surface grinding method of the grinding aggregate is any one, two, or three of cutting saw grinding, grinding wheel grinding and sandpaper grinding, the grinding time of each surface grinding method is more than 30s, and the grinding degree of each aggregate sample in the polished aggregate is the same.

3. The method for testing surface energy of aggregate based on static drop method according to claim 2, wherein the specific steps of the pretreatment are: after the surface of the polished aggregate is polished, rinsing it with distilled water until no sediment is attached to the surface, and drying the cleaned aggregate sample at 110-120° C.

4. The method for testing surface energy of aggregate based on static drop method according to claim 1, wherein the specific steps of using static drop method to test contact angle of the polished aggregate are:
   starting an optical contact angle meter and preheating, fixing the polished aggregate in the test chamber uniformly, and setting the grinding surface of each aggregate sample in the polished aggregate to face the camera of the optical contact angle meter;
   adjusting the reagent needle to a preset position and releasing the droplets of different test reagents;
   moving the test chamber so that each aggregate sample corresponds to receive one of the released droplets;
   testing the contact angle between each aggregate sample and the received droplet for a preset test time.

5. The method for testing surface energy of aggregate based on static drop method according to claim 4, wherein the specific steps for adjusting the reagent needle to the preset position are:
   drawing the test reagent into a needle tube, moving the position of the reagent needle until a distance of a drop is maintained between the needle and the aggregate sample, and both the needle and the aggregate sample appear in the camera picture;
   the specific steps of releasing droplets of different test reagents are:
   controlling the pressure of the needle tube, so that different test reagents release droplets of the same volume, and the released droplets are attached to the tip of the needle, wherein the different test reagents included distilled water, formamide, and ethylene glycol, and each needle released a droplet of one test reagent.

6. The method for testing surface energy of aggregate based on static drop method according to claim 5, wherein the specific steps for testing the contact angle between each aggregate sample and the received droplet within the preset test time are as follows:
   on the surface of the aggregate sample, the intersection of the received droplet and its projection is set as the baseline, and using an optical contact angle meter to measure the angle between the tangent at the intersection of the droplet profile and the baseline, which is recorded as contact angle, obtaining the contact angles between the polished aggregate and different test reagents.

7. The method for testing surface energy of aggregate based on static drop method according to claim 6, when using distilled water as the test reagent, the preset test time of the contact angle is 10-30s;
   when using formamide or ethylene glycol as the test reagent, the preset test time of the contact angle is greater than 20s.

8. The method for testing surface energy of aggregate based on static drop method according to claim 1, wherein the specific steps for obtaining the functional relationship between the surface texture index and the surface energy by fitting are:
   fitting the surface energy of the polished aggregate and the surface texture index of the polished aggregate exponentially to obtain a functional relationship between the surface texture index and the surface energy, the specific functional relationship is:

$$\gamma = Ae^{Kx}$$

where $\gamma$ is aggregate surface energy considering the influence of surface texture, the unit is erg/cm$^2$, x is the surface texture index of the aggregate; A is the surface energy corresponding to the surface texture index of the aggregate in the state of x=0, the unit is erg/cm$^2$; K is a constant that determines the influence of the surface texture on the surface energy;
   in the exponential fitting process, obtaining parameters A and K, and determining the functional relationship between the surface texture index and surface energy.

* * * * *